United States Patent [19]

Fleckenstein et al.

[11] Patent Number: 5,043,485

[45] Date of Patent: Aug. 27, 1991

[54] PROCESS FOR THE HYDROGENATION OF FATTY ACID METHYL ESTER MIXTURES

[75] Inventors: Theo Fleckenstein, Hilden; Joachim Pohl, Duesseldorf; Franz J. Carduck, Haan, all of Fed. Rep. of Germany

[73] Assignee: Henkel Kommanditgesellschaft auf Aktien, Duesseldorf-Holthausen, Fed. Rep. of Germany

[21] Appl. No.: 464,606

[22] Filed: Jan. 11, 1990

Related U.S. Application Data

[63] Continuation of Ser. No. 222,455, Jul. 21, 1988, abandoned.

[30] Foreign Application Priority Data

Jul. 22, 1987 [DE] Fed. Rep. of Germany .... 37 24 257

[51] Int. Cl.$^5$ .................. C07C 29/136; C07C 31/125
[52] U.S. Cl. ..................................... 568/885; 502/241
[58] Field of Search ........................................ 568/885

[56] References Cited

U.S. PATENT DOCUMENTS

| | | | |
|---|---|---|---|
| 2,080,419 | 5/1937 | Green | 568/885 |
| 2,091,800 | 8/1937 | Adkins et al. | 568/885 |
| 2,094,127 | 9/1957 | Lazier | 568/885 |
| 2,109,844 | 3/1938 | Lazier | 568/885 |
| 3,173,959 | 3/1965 | Rittmeister et al. | 568/885 |
| 3,180,898 | 4/1965 | Eisenlohr et al. | 568/285 |
| 3,193,586 | 7/1965 | Rittmeister | 260/638 |
| 4,113,662 | 9/1978 | Wall | 252/473 |
| 4,199,479 | 4/1980 | Wilkes | 252/457 |
| 4,433,175 | 2/1984 | Kaufhold | 568/885 |
| 4,482,766 | 11/1984 | Stönner | 568/885 |
| 4,611,085 | 9/1986 | Kitson | 508/885 |
| 4,652,685 | 3/1987 | Cawse et al. | 568/885 |

FOREIGN PATENT DOCUMENTS 2613226 12/1978 Fed. Rep. of Germany .
2513377 8/1985 Fed. Rep. of Germany .
124510 3/1971 India .

OTHER PUBLICATIONS

Ulmanns Encyklopaedie der Technischen Chemie, 4th Edition, vol. 11, pp. 427–445.

Primary Examiner—J. E. Evans
Attorney, Agent, or Firm—Ernest G. Szoke; Wayne C. Jaeschke; Daniel S. Ortiz

[57] ABSTRACT

In the catalytic hydrogenation of fatty acid methyl ester mixtures, the mixtures are continuously reacted with hydrogen under pressures of from 100 to 300 bar and at temperatures of from 160° to 270° C. with molar ratios or hydrogen to fatty acid methyl ester mixture of from 10:1 to 500:1. The reaction is carried out over catalysts which contain from 30 to 40% by weight copper, from 23 to 30% by weight chromium, from 1 to 10% by weight manganese, from 1 to 10% by weight silicon and from 1 to 7% by weight barium (% by weight, based in each case on total weight of the oxidic catalyst) and, if desired, other transition metals in the form of their oxides. After calcination of the components, the catalyst is converted into shaped particulate and/or granulated elements with from 1 to 10% by weight, based on oxidic catalyst, of at least one binder in addition to 1 to 10% by weight graphite. The catalyst is activated with hydrogen or a hydrogen-containing gas mixture. This process enables production of fatty alcohols in high yield from fatty acid methyl ester mixtures containing fatty acid residues in the $C_8$ to $C_{22}$ carbon chain range without prior separation of the mixtures into individual boiling fractions.

16 Claims, No Drawings

PROCESS FOR THE HYDROGENATION OF FATTY ACID METHYL ESTER MIXTURES

This application is a continuation of application Ser. No. 07/222,455 filed 7/21/88, now abandoned.

BACKGROUND OF THE INVENTION

1. Field of the Invention

This invention relates to a new process for the catalytic hydrogenation of fatty acid methyl ester mixtures using particulate and/or granulated catalysts containing copper chromite under pressures in the range from 100 to 300 bar.

2. Description of Related Art

Fatty alcohols, i.e., predominantly linear, monofunctional alcohols having chain lengths of 8 and more carbon atoms, and their production are described in detail in the literature, for example in Ullmanns Encyklopaedie der technischen Chemie, 4th Edition, Vol. 11, pages 427 to 445. A preferred starting material for their production are the fatty acids and fatty acid mixtures occurring in natural fats and/or oils which may be converted into fatty alcohols of corresponding chain length by catalytic hydrogenation. Through the use of the fatty acids to be reduced in the form of their methyl esters, the catalysts in particular are protected against aggressive attack by the free carboxyl group, so that industrial processes can be operated for sufficiently long periods with satisfactory volume-time yields. Today, therefore, the predominant quantity of native fatty alcohols is produced from fatty acid methyl esters by the gas-phase hydrogenation process in which the distilled methyl esters are passed in the vapor phase, together with a large excess of hydrogen, over a fixed bed of copper-containing mixed oxide catalysts, such as, for example, copper chromite spinel catalysts, at temperatures above 200° C. and under pressures of from about 250 to 300 bar.

The copper-mixed oxide catalysts obtained by co-precipitation via the wet route are used as particulate catalysts or extrudates and before use are generally reduced in the plant or installation.

According to the relevant patent literature, fatty acid esters, more especially fatty acid methyl esters, and free fatty acids are therefore simultaneously used as starting materials for the hydrogenation reaction to saturated and/or unsaturated fatty alcohols, for example, as described in German Patent Publications DE-PSS 965 236, 10 05 497, 25 13 377 and 26 13 226. U.S. Pat. Nos. 4,113,662, 4,482,766, and 4,199,479 as well as Indian Patent 124510 also describe pertinent process features. As far as industrial application is concerned, the proposals mentioned are evaluated entirely differently according to whether the fatty acid esters or the free fatty acids are used as starting material for the hydrogenation.

According to the present state of the hydrogenation art, the methyl esters are separated by distillation, after transesterification of the oils and fats and after separation of the glycerol, into a boiling cut in the 8 to 10 carbon chain range and into a boiling cut in the 12 to 18 carbon chain range to enable the hydrocarbons automatically accumulating to be removed during the subsequent hydrogenation of the methyl esters. The two fractions are separately hydrogenated, the quality-reducing hydrocarbons being distilled off overhead. Since the boiling ranges of the hydrocarbons overlap those of the short-chain fatty alcohols, the fatty acid methyl esters must be separated according to the present state of the art. In addition, the reaction velocity in the hydrogenation of short-chain fatty acid methyl esters is lower than in the hydrogenation of long-chain fatty acid methyl esters. Accordingly, fatty acid methyl esters in the 14 to 16 carbon chain range are overhydrogenated when co-hydrogenated with shorter-chain fatty acid methyl esters. The carbon chain ranges separated are normally hydrogenated at different space flow velocities.

DESCRIPTION OF THE INVENTION

Other than in the operating examples, or where otherwise indicated, all numbers expressing quantities of ingredients or reaction conditions used herein are to be understood as modified in all instances by the term "about".

It has been found surprisingly that it is possible with certain highly active and selective long-life catalysts containing copper chromite as the principal constituent to control the hydrogenation of fatty acid methyl esters in such a way that the formation of hydrocarbons is largely suppressed and relatively short-chain and relatively long-chain fatty acid methyl esters can be hydrogenated at one and the same time.

An object of the present invention is to provide a process for the catalytic hydrogenation of fatty acid methyl ester mixtures using particulate and/or granulated catalysts containing copper chromite, by which fatty acid methyl ester mixtures containing short-chain and long-chain fatty acid residues in the C8 to C22 carbon chain range can be reacted to fatty alcohols in high yields without any need for the fatty acid methyl ester mixtures to be separated beforehand into individual boiling cuts. The heterogeneous transition-metal catalyst used for the reaction leads to the required products with high activity and selectivity without secondary reactions significantly contributing to a reduction in the product yield. Together with the establishment of moderate reaction conditions, this improves the economy of the process in relation to the prior art.

The formation of hydrocarbons is minimal because, when the mixtures of fatty alcohols are worked up by distillation, the boiling ranges of the hydrocarbons overlap those of the short-chain fatty alcohols.

The present invention relates to a process for the catalytic hydrogenation of fatty acid methyl ester mixtures containing short-chain and long-chain fatty acid residues in the $C_8$ to $C_{22}$ carbon chain range at elevated reaction temperatures using particulate and/or granulated catalysts containing copper chromite as principal constituent, which comprises continuously reacting the fatty acid methyl ester mixtures containing short- and long-chain fatty acid residues with $C_8$–$C_{22}$ range with hydrogen under pressures of 100 to 300 bar and at temperatures of from 160 to 270° C. with molar ratios of hydrogen to fatty acid methyl ester substrate of from 10:1 to 500:1. The reaction is carried out over catalysts which contain from 30 to 40% by weight copper, from 23 to 30% by weight chromium, from 1 to 10% by weight manganese and from 1 to 7% by weight barium (% by weight, based in each case on oxidic catalyst mass) and, if desired, other transition metals in the form of their oxides and which, after calcination of the components forming the catalyst mass, have been converted into shaped particulate and/or coarse-grained elements with from 1 to 10% by weight, based on oxidic catalyst, of at least one binder in addition to 1 to 10% by weight graphite and activated with hydrogen or a hydrogen-containing gas mixture.

Fatty acid methyl ester mixtures suitable for catalytic hydrogenation by the process of this invention can be of native or synthetic origin. Suitable starting materials for the hydrogenation process according to the invention are the fats, train oils or oils emanating from animal or vegetable sources in which mono- or polyunsaturated fatty acids are esterified with glycerol, the fatty acid residues optionally having the same or different degrees of saturation and alkyl chain lengths. The fatty acid methyl esters are obtained by transesterification in known manner from the above-mentioned fats, train oils and oils.

Fatty acid methyl ester mixtures in the context of the present invention consist of fatty acid methyl esters which are linear and/or branched, saturated and/or unsaturated and have a carbon chain length of 8 to 22 carbon atoms.

In the process of this invention, the catalytic hydrogenation of the fatty acid methyl ester mixtures is carried out in the presence of a catalyst which contains (based on the oxidic catalyst mass) from 30 to 40% by weight copper, from 23 to 30% by weight chromium, from 1 to 10% by weight manganese, from 1 to 7% by weight barium, and, optionally, other transition metals. The metals mentioned are present in the form of their oxides after production of the catalyst masses which is carried out by methods known in the prior art. Oxide formation takes place, as is known from the prior art, during the so-called "calcination," i.e. by thermal decomposition of mineral salts of the particular metals.

In the process of this invention, a catalyst containing from 1 to 10% by weight $SiO_2$, based on the oxidic catalyst mass, is used for the hydrogenation of the fatty acid methyl ester mixtures.

In one preferred embodiment of the process of this invention, fatty acid methyl ester mixtures are continuously hydrogenated using a catalyst advantageously containing from 32 to 38% by weight copper, based on the oxidic catalyst mass. It is also advantageous to adjust the quantity of chromium in the catalyst to a range of from 26 to 29% by weight, the quantity of manganese to a range of from 1 to 10% by weight, the quantity of barium to a range of from 1.5 to 3% by weight and the quantity of silicon to a range of from 1.5 to 3% by weight, based in each case, on the oxidic catalyst mass before activation. In one particularly preferred embodiment, a catalyst containing 36% by weight copper, 29% by weight chromium, 2.5% by weight manganese, 1.7% by weight barium and 1.0% by weight silicon, based in each case on the oxidic catalyst mass before activation, and optionally other transition metals in the form of their oxides is used for the catalytic hydrogenation of fatty acid methyl esters. With the catalysts as described herein, it is possible to obtain considerable increases in activity. For this reason, the use of said catalysts in the process of this invention is regarded as particularly preferred.

In another preferred embodiment of the process of this invention, a catalyst containing other transition metals in the form of their oxides in addition to the above-mentioned quantities of copper, chromium, manganese, barium and silicon is used for the catalytic hydrogenation of fatty acid methyl ester mixtures. Thus, it is possible to use a catalyst containing from 1 to 5% by weight and, preferably, from 2 to 3% by weight each of zirconium and/or cerium in addition to the metals described above. In this connection, it is possible to add one of the transition metals mentioned in the form of its oxides or even several of the transition metals mentioned in the form of their oxides in admixture with one another to the catalysts in accordance with this invention. The use of additionally doped catalysts such as described in the process of this invention leads to a considerable increase in the activity and selectivity of the catalysts, particularly where hydrogenation is carried out in a trickling bed.

Catalysts employed in the process of this invention preferably contain from 1 to 10% by weight of graphite to improve the processibility of the granulates and/or extrudates. A quantity of 5% by weight of graphite is most preferably added to and thoroughly mixed with the calcined powder-form material before granulation.

According to the invention, an improvement in the process is obtained by bringing the catalyst containing the above-mentioned metals in the form of their oxides and graphite into granulate or extrudate form using from 1 to 10% by weight of one or more binders and preferably 10% by weight of one or more binders. Suitable binders are compounds known for this purpose from the prior art, of which either one or even several are used in the catalyst employed in accordance with the process of this invention. The use of one or more binders selected from polyvinyl acetate and methyl methacrylate has proved to be particularly effective. In contrast to numerous, non-free-flowing catalyst materials known from the prior art, it was possible to provide a catalyst in granulate or extrudate form for the process of this invention, of which the loosened, porous structure contributes significantly to increasing the activity and selectivity of the catalyst in the hydrogenation of the fatty acid methyl ester mixtures, particularly in a trickling bed. Polyvinyl acetate is preferably used as binder for the production of the catalyst granulates or extrudates. Commercially obtainable 40% by weight polyvinyl acetate suspensions, for example, are used for the production of the catalyst. After thorough mixing, polyvinyl acetate suspensions are added in small quantities to the calcined, powder-form catalyst materials and mixed therewith until agglomerate grains begin to build up. The agglomerate-containing powder is then compacted to small granulates, for example, in a perforated-roll granulator. These techniques are known from the prior art. The granulates are dried in known manner to residual moisture contents of from 10 to 15%. The granulates resulting from this operation are sieved and grain fractions of a certain grain size are sieved out for the practice of the process of this invention. Catalyst grain fractions having a grain size of from 0.6 to 3 mm are advantageously used where the process of this invention is used for the catalytic hydrogenation of fatty acid methyl ester mixtures in trickling beds.

The catalysts can be compressed into tablet form, for example, into $4 \times 4$ mm tablets. For hardening, the tablets are tempered in air for 6 h at a temperature of 200°–280° C. The specific surface as determined by the BET method (Z. Anal. Chem. 288 (1968), 187–193) was $40 \pm 10$ m$^2$/g.

The granulated catalysts suitable for use in the process of this invention for the hydrogenation of fatty acid methyl ester mixtures have a specific surface of 30 to 50 m$^2$/g. The described form of pregranulation leads to a special, loosened pore structure which increases the degree of pore utilization.

In the practice of the process of this invention for the hydrogenation of fatty acid methyl ester mixtures, it has been found to be of particular advantage to react the fatty acid methyl ester mixtures with hydrogen in the presence of a catalyst of which the granulates, extrudates or tablets have a diameter of from 1 to 6 mm and a length of from 1 to 6 mm. Such granulates or extrudates (tablets) show excellent activity and selectivity in the reaction of the fatty acid methyl ester mixtures with hydrogen to long-chain fatty alcohols and, in addition, can be readily separated from the reaction products. In addition, the useful lives obtainable with such catalysts are considerably better than the useful lives of the catalysts known from the prior art. In addition, prior catalysts have the disadvantage that, in some cases, they disintegrate during the reaction and as a result can be separated from the reaction products only with considerable difficultly.

Another factor significantly affecting the activity and selectivity of the catalysts used in accordance with the process of this invention is the pore volume of the shaped catalyst elements. It has been found that the pore volume of the catalysts useable in accordance with the invention must be in an optimal range to produce optimal results in the process of this invention for the hydrogenation of fatty acid methyl ester mixtures. In one preferred embodiment, metal-containing catalysts are used where the pore volume is in the range from 0.4 to 0.6 cm/g. A pore volume in this range also has the advantage of contributing to increasing the activity and selectivity of the hydrogenation catalysts. High activities and selectivities are obtained both in trickling bed reactors and in sump phase reactors. At the same time, the catalysts as described herein have an extremely long useful life in the process of this invention and do not present problems during the separation of catalyst and reaction products.

The catalysts used in the process of this invention are activated with hydrogen or with a hydrogen-containing gas mixture before they are used in the hydrogenation of fatty acid methyl ester mixtures. For reasons of economy, a gas mixture predominantly consisting of a nitrogen/hydrogen gas mixture is advantageously used for activation of the catalyst. As known from the prior art, such activation is advantageously carried out by drying the catalyst in a stream of nitrogen at elevated temperature after their production and adding hydrogen in increasing quantities to the drying gas for activation. The proportion of hydrogen in the activating gas mixture is maintained between 0.1 and 10% by volume. The activation of the catalysts is carried out both in situ and optionally in a vessel separate from the reaction vessel.

The reaction temperatures in the hydrogenation of fatty acid methyl ester mixtures in accordance with the process of the present invention are maintained in the range from 160° to 270° C. and, preferably, in the range from 180° to 240° C. In the temperature control of the reaction, a general factor to be taken into consideration is that the hydrogenation of the fatty acid methyl ester mixtures to corresponding fatty alcohols is an exothermic chemical reaction. Accordingly, in the control of the reaction temperature, it is important to ensure that the heat of reaction generated is dissipated in an appropriate manner.

The process of this invention for the hydrogenation of fatty acid methyl ester mixtures is also characterized in that the molar ratio of hydrogen to fatty acid residue in the fatty acid methyl ester substrate is adjusted to a value of from 10:1 to 500:1. Accordingly, the throughput of hydrogen gas, as measured in mol/hour, is from 10 to 500 times higher than the throughput of fatty acid methyl ester, as measured in mol fatty acid residue/hour.

A major advantage of the process of this invention includes the ability to produce fatty alcohols from transesterified mixtures of fatty acid methyl esters containing residues of fatty acids without any need for separation beforehand into the individual boiling cuts.

This saves capital expenditure on intermediate storage tanks and additional fractionating columns. In addition, a higher net product is obtained by virtue of the greater selectivity of the catalyst compared with the catalyst hitherto used.

The invention is illustrated by the following examples.

EXAMPLES

PRODUCTION EXAMPLE

Production of a catalyst 84.93 g $Ba(NO_3)_2$, 3493 g $Cu(NO_3)_2 \cdot 2\ H_2O$, 294.43 g $Mn(NO_3)_2 \cdot 4\ H_2O$ and 62.3 g $SiO_2$ in the form of a 40% by weight silica sol were dissolved with vigorous stirring in 9 liters deionized water at temperatures of from 30° to 90° C. In a second vessel, 1639 g $CrO_3$ were dissolved in 9 liters deionized water under the same conditions, followed by the addition of 3650 g of a 25% ammonia solution. The solution containing barium, manganese and copper was then pumped at 30° to 90° C. into the ammonium chromate solution, a mixture of barium chromate, manganese hydroxide, silicon hydroxide and copper chromate being precipitated from the solution. Precipitation stopped when the pH value fell below 7.

The precipitate was filtered in a frame filter press and washed with deionized water until free from nitrate. The filter cake was dried overnight at 90° to 120° C. and then reduced to a coarse powder in a cutting mill. The resulting chromate powder was thermally decomposed ("calcined") to chromite at 300° to 500° C. in a revolving tube furnace. The calcined powder-form material had the following chemical composition:

Cu: 38±0.5%
Cr: 29±0.5%
Mn: 2.5±0.5%
Ba: 1.9±0.5% and
Si: 1±0.3%

5% by weight graphite was added to 1 liter of the powder, followed by mixing for 15 minutes in a Loedige mixer. 10% by weight of a 40% by weight polyvinyl acetate suspension were then added, followed by brief mixing until agglomerates began to build up. The powder was then compacted to small granulates in a perforated-roll granulator, dried to a residual moisture content of 10 to 15% and sieved to a 0.6 to 1.2 mm grain fraction.

The granulate had excellent flow properties and could be compressed in a rotary tabletting machine to tablets 3 to 6 mm in diameter and 2 to 4 mm thick.

After hardening of the tablets (6h, 200° C, in air), the specific BET surface was 40±10 m²/g for a pore volume of from 0.4 to 0.6 cm²/g.

EXAMPLES 1 to 3

0.5 liter of the catalyst prepared and granulated in accordance with the Production Example (mean grain size 1 mm) were introduced into a reaction tube 1 liter in volume with an internal diameter of 25 mm to which 2 mm glass beads were then added in order uniformly to disperse the liquid phase.

After drying and reduction of the catalyst in a stream of nitrogen/hydrogen (max. hydrogen concentration 1%, max. temperature 200° C.), hydrogen was continuously passed downwards through the reactor at 250 bar/200°–220° C. in co-current with a fatty acid methyl ester mixture which had a C-chain distribution of $C_8$ to $C_{18}$, corresponding to the fatty acids present in the coconut oil, and the liquid reaction product was collected in a two-stage separation system. The reaction conditions and the product analyses are shown in Table 1:

TABLE 1

Test Results
Hydrogenation of coconut oil methyl ester ($C_8$–$C_{18}$)

| Pressure: 250 bar | Acid value (a.v.) = <1 | | |
|---|---|---|---|
| Saponification value (s.v.): 249 | Iodine value (i.v.) = 8.2 | | |
| | Hydroxyl value (OH.v.) = 19.0 | | |
| Examples | 1 | 2 | 3 |
| Reaction temperature (°C.) | 200 | 200 | 200 |
| LHSV* ($1 \times 1^{-1} \times h^{-1}$) | 2.0 | 3.0 | 4.0 |
| H2: substrate (mol × mol$^{-1}$) | 100 | 75 | 50 |
| Saponification value of product | 0.3 | 0.8 | 12 |
| Product composition (% by weight) | | | |
| Fatty acid methyl esters | 0.1 | 0.3 | 4.7 |
| Fatty alcohols | 85.9 | 85.7 | 81.9 |
| Hydrocarbons | 0.05 | 0.03 | 0.03 |
| Methanol | 13.9 | 13.9 | 13.3 |

LHSV* (liquid hourly space velocity)

COMPARISON EXAMPLES 1 to 3

The coconut oil methyl ester fractions in the boiling range of the $C_8$ to $C_{10}$ and the $C_{12}$ to $C_{14}$ methyl esters and of the tallow fatty acid methyl esters ($C_{16}$ to $C_{18}$) were hydrogenated under the reaction conditions described in Table 2. The tests were carried out in the same reactor and with the same catalyst as in Example 1.

TABLE 2

Test Results
Hydrogenation of coconut oil methyl esters

| Pressure: 250 bar | | | |
|---|---|---|---|
| Comparison Examples | 1 | 2 | 3 |
| Substrate (fraction) | $C_8$–$C_{10}$ | $C_{12}$–$C_{18}$ | $C_{16}$–$C_{18}$ |
| Reaction temperature (°C.) | 200 | 200 | 200 |
| LHSV* ($1 \times 1^{-1} \times h^{-1}$) | 4.0 | 2.0 | 4.0 |
| H2: substrate (mol × mol$^{-1}$) | 50 | 100 | 50 |
| Saponification value of product | 35 | 0.4 | 0.8 |
| Product composition (% by weight) | | | |
| Fatty acid methyl esters | 11.7 | 0.2 | 0.4 |
| Fatty alcohols | 70.6 | 86.3 | 87.6 |
| Hydrocarbons | 0.02 | 0.05 | 0.03 |
| Methanol | 17.6 | 13.4 | 11.95 |

A can be seen from Comparative Example 1, methyl esters of short-chain fatty acids cannot be hydrogenated as well as those of relatively long-chain fatty acids (comparison basis: volume substrate/volume catalyst/hour). Examples 1 to 3 show that the hydrogenation of unfractionated coconut oil methyl esters does not lead to any deterioration in selectivity in respect of hydrocarbon formation, despite differences in the reactivity of the individual methyl esters. Under the indicated reaction conditions, the hydrocarbon contents are distinctly below 0.1% by weight, so that there is no need for separation by distillation.

We claim:

1. A process for the catalytic hydrogenation of fatty acid methyl ester mixtures which comprises the steps of:
   A. continuously reacting fatty acid methyl ester mixtures containing short-chain and long-chain fatty acid residues in the $C_8$ to $C_{22}$ carbon chain range with hydrogen at a pressure of from about 100 to about 300 bar and a temperature of from about 160° to about 270° C. at a molar ratio of hydrogen to fatty acid residues in the fatty acid methyl ester substrate of from about 10:1 to about 500:1 in the presence of a particulate and/or granulated calcined oxidic catalyst activated by hydrogen or hydrogen containing gas and prepared from a mixture containing from about 30 to about 40% by weight copper, from about 23 to about 30% by weight chromium, from about 1 to about 10% by weight manganese, from about 1 to about 10% by weight silicon from about 1 to about 7% by weight barium, from 1 to 10% by weight of at least one binder and from about 1 to about 10% by weight graphite the percentages by weight being based on the total weight of the oxidic catalyst to form a reaction product containing a mixture of fatty alcohols and methanol, and
   B. separating the reaction product from the catalyst.
2. The process of claim 1 wherein said catalyst contains from about 32 to about 38% by weight copper.
3. The process of claim 1 wherein said catalyst contains from about 26 to about 29% by weight chromium.
4. The process of claim 1 wherein said catalyst contains from about 1.5 to about 3% by weight barium.
5. The process of claim 1 wherein said catalyst contains from about 1.5 to about 3% by weight silicon.
6. The process of claim 1 wherein said catalyst contains from about 32 to about 38% by weight copper, from about 26 to about 29% by weight chromium, from about 1 to about 6% by weight manganese, from about 1.5 to about 3% by weight barium, and from about 1.5 to about 3% by weight silicon.
7. The process of claim 1 wherein said catalyst contains from about 32 to about 38% by weight copper, from about 26 to about 29% by weight chromium, from about 1 to about 6% by weight manganese, from about 1.5 to about 3% by weight barium, from about 1.5 to about 3% by weight silicon, and from about 1 to about 5% by weight of at least one of zirconium and cerium.
8. The process of claim 7 wherein said catalyst contains from about 2 to about 3% by weight of at least one of said zirconium and cerium.
9. The process of claim 1 wherein said binder is selected from polyvinyl acetate and methyl methacrylate.
10. The process of claims 1 wherein said catalyst has a grain size of from about 0.6 to about 3.0 mm.
11. The process of claims 1 wherein said particulate and/or granulated catalyst has a diameter of from about 1 to about 6 mm and a length of from about 1 to about 6 mm.
12. The process of claims 1 wherein said catalyst has a specific surface of from about 30 to about 50 m$^2$/g.
13. The process of claims 1 wherein said catalyst has a pore volume of from about 0.4 to about 0.6 cm$^3$/g.
14. The process of claims 1 wherein said catalyst is activated with an N$_2$/H$_2$ gas mixture containing from about 0.1 to about 10% by volume hydrogen.
15. The process of claim 1 wherein the reaction temperature is maintained between about 180° to about 240° C.
16. The process of claim 1 wherein said catalytic hydrogenation is carried out in a trickling bed reactor.

* * * * *